(12) United States Patent
Farmer et al.

(10) Patent No.: US 10,016,844 B2
(45) Date of Patent: Jul. 10, 2018

(54) CHEMICAL, BIOLOGICAL, AND RADIOACTIVE CONTAMINATION REMEDIATION WITH LASERS

(71) Applicant: LAWRENCE LIVERMORE NATIONAL SECURITY, LLC, Livermore, CA (US)

(72) Inventors: Joseph C. Farmer, Tracy, CA (US); Alexander M. Rubenchik, Livermore, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 243 days.

(21) Appl. No.: 14/599,051

(22) Filed: Jan. 16, 2015

(65) Prior Publication Data

US 2016/0207077 A1    Jul. 21, 2016

(51) Int. Cl.
| | | |
|---|---|---|
| *B23K 26/08* | (2014.01) | |
| *B23K 26/36* | (2014.01) | |
| *G01V 5/00* | (2006.01) | |
| *G01T 7/02* | (2006.01) | |
| *G01V 5/02* | (2006.01) | |
| *G01T 7/00* | (2006.01) | |
| *G01N 1/04* | (2006.01) | |
| *B08B 7/00* | (2006.01) | |
| *B08B 15/02* | (2006.01) | |

(Continued)

(52) U.S. Cl.
CPC ........ *B23K 26/0884* (2013.01); *B08B 7/0042* (2013.01); *B08B 15/02* (2013.01); *B23K 26/36* (2013.01); *G01N 1/04* (2013.01); *G01T 7/00* (2013.01); *G01T 7/02* (2013.01); *G01V 5/0091* (2013.01); *G01V 5/02* (2013.01); *G21F 9/005* (2013.01); *G01N 2001/021* (2013.01); *G01N 2001/028* (2013.01)

(58) Field of Classification Search
CPC ................ B23K 26/0884; B23K 26/36; B23K 26/0869; B23K 26/0876; B23K 26/14; B23K 26/142; B23K 26/16; G01N 1/04; G01N 2001/021; G01N 2001/028; G01N 2001/045; G01T 7/00; G01T 7/02; G01V 5/0091; G01V 5/02
See application file for complete search history.

(56) References Cited

U.S. PATENT DOCUMENTS

| | | | |
|---|---|---|---|
| 4,267,445 A | 5/1981 | Cabbiness et al. | |
| 6,288,362 B1 * | 9/2001 | Thomas | B08B 7/0042 134/1 |

(Continued)

FOREIGN PATENT DOCUMENTS

WO    2014113293    7/2014

OTHER PUBLICATIONS

American Nuclear Society, Fukushima Daiichi, ANS Committee Report, www.ang.org, 2012, 45 pp.

*Primary Examiner* — Saeed T Chaudhry
(74) *Attorney, Agent, or Firm* — Eddie E. Scott

(57) ABSTRACT

A laser is used to clean surfaces contaminated with chemical, biological, or radioactive substances. The laser directs a laser beam onto the surfaces and the ejecta is collected by a getter which can be a version of vacuum cleaner. A mobile system includes a laser transporting arm and collection system used in cleanup of metal and concrete surfaces contaminated with chemical, biological, or radioactive substances.

2 Claims, 4 Drawing Sheets

(51) Int. Cl.
   *G21F 9/00* (2006.01)
   *G01N 1/02* (2006.01)

(56) References Cited

U.S. PATENT DOCUMENTS

| | | |
|---|---|---|
| 9,250,353 B2 * | 2/2016 | Mariella, Jr. ........ G01V 5/0091 |
| 2006/0097171 A1 | 5/2006 | Balchunas et al. |
| 2016/0158817 A1 * | 6/2016 | Zediker ................. C10G 75/00 134/1 |

* cited by examiner

CHEMICAL, BIOLOGICAL, AND RADIOACTIVE CONTAMINATION REMEDIATION WITH LASERS

STATEMENT AS TO RIGHTS TO APPLICATIONS MADE UNDER FEDERALLY SPONSORED RESEARCH AND DEVELOPMENT

The United States Government has rights in this application pursuant to Contract No. DE-AC52-07NA27344 between the United States Department of Energy and Lawrence Livermore National Security, LLC for the operation of Lawrence Livermore National Laboratory.

CROSS-REFERENCE TO RELATED APPLICATIONS

This application discloses apparatus, systems, and methods that have similarities to apparatus, systems, and methods disclosed in U.S. patent application Ser. No. 14/589,150 filed Jan. 5, 2015 entitled "Nuclear Radiation Cleanup and Uranium Prospecting."

BACKGROUND

Field of Endeavor

The present application relates to chemical, biological, and radioactive contamination remediation and more particularly to chemical, biological, and radioactive contamination remediation with lasers.

State of Technology

This section provides background information related to the present disclosure which is not necessarily prior art.

Surface contamination by chemical, biological, or radioactive material is not unusual. Generally, the only very thin subsurface layer of metal is contaminated. The penetration can be deeper in concrete due to the small cracks and voids. Typically, the total amount of contaminant is small. Typical decontamination includes the surface cleaning or contaminated structure demolition. In both cases a huge amount of dangerous waste is produced. The storage of the waste is a big problem. In both the Three-Mile Island and Fukushima nuclear accidents, scabbling of contaminated concrete was important for the removal of the radioactive waste material. The handling of chemical and biological contaminated waste material presents major problems. The mechanical cleaning of contaminated surfaces produces waste that creates environmental and health problems.

SUMMARY

Features and advantages of the disclosed apparatus, systems, and methods will become apparent from the following description. Applicant is providing this description, which includes drawings and examples of specific embodiments, to give a broad representation of the apparatus, systems, and methods. Various changes and modifications within the spirit and scope of the application will become apparent to those skilled in the art from this description and by practice of the apparatus, systems, and methods. The scope of the apparatus, systems, and methods is not intended to be limited to the particular forms disclosed and the application covers all modifications, equivalents, and alternatives falling within the spirit and scope of the apparatus, systems, and methods as defined by the claims.

The disclosed apparatus, systems, and methods utilize a laser to clean surfaces contaminated with chemical, biological, and radioactive substances. A laser beam is directed onto the surfaces and the ejecta is collected by a getter (e.g. a version of vacuum cleaner). The system includes detectors visualizing the level of contaminant. Multiple layers of ablation are utilized to complete surface cleaning. A mobile system includes a laser transporting arm and collection system. The disclosed apparatus, systems, and methods have use in cleanup of metal and concrete surfaces contaminated with chemical, biological, and radioactive substances.

The apparatus, systems, and methods are susceptible to modifications and alternative forms. Specific embodiments are shown by way of example. It is to be understood that the apparatus, systems, and methods are not limited to the particular forms disclosed. The apparatus, systems, and methods cover all modifications, equivalents, and alternatives falling within the spirit and scope of the application as defined by the claims.

BRIEF DESCRIPTION OF THE DRAWINGS

The accompanying drawings, which are incorporated into and constitute a part of the specification, illustrate specific embodiments of the apparatus, systems, and methods and, together with the general description given above, and the detailed description of the specific embodiments, serve to explain the principles of the apparatus, systems, and methods.

DETAILED DESCRIPTION OF SPECIFIC EMBODIMENTS

Figure 1:
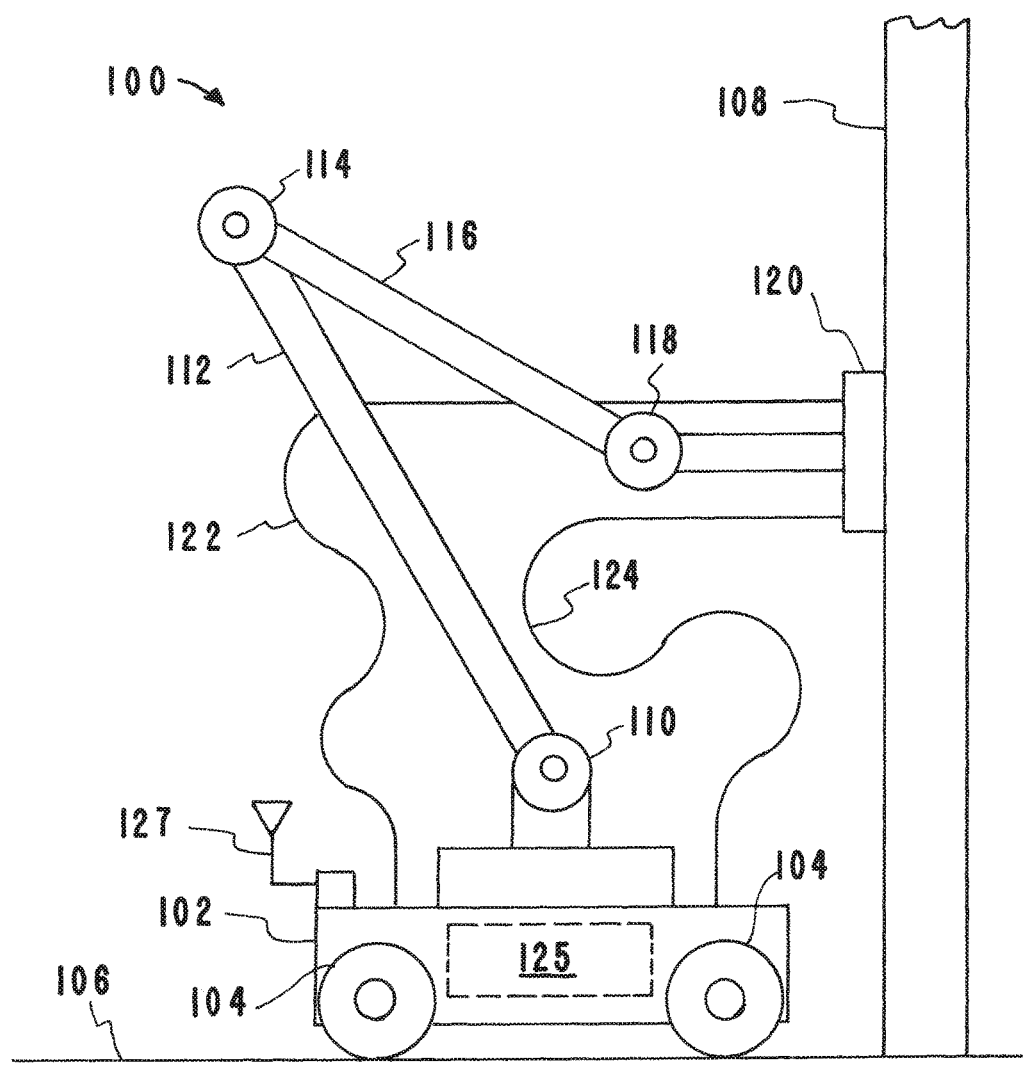
FIG. 1 illustrates a robot that can be used to clean a surface contaminated with radioactive substances.

Referring to the drawings, to the following detailed description, and to incorporated materials, detailed information about the apparatus, systems, and methods is provided including the description of specific embodiments. The detailed description serves to explain the principles of the apparatus, systems, and methods. The apparatus, systems, and methods are susceptible to modifications and alternative forms. The application is not limited to the particular forms disclosed. The application covers all modifications, equivalents, and alternatives falling within the spirit and scope of the apparatus, systems, and methods as defined by the claims.

Remediation of Radioactive Contaminated Surfaces

Surface contamination by radioactive material is not unusual. Generally, the only very thin subsurface layer of metal is contaminated. The penetration can be deeper in concrete due to the small cracks and voids. Typical decontamination includes the surface cleaning or contaminated structure demolition. In both cases a huge amount of dangerous waste is produced. The storage of the waste is a big problem. In both the Three-Mile Island and Fukushima nuclear accidents, scabbling of contaminated concrete was important for the removal of the radioactive waste material. A damaged nuclear power plant is an example of contamination by radioactive material. The reactor building includes floors, walls, the reactor vessel, and other structures that are contaminated with radioactive material: In order to access the inside of the damaged reactor building, an opening in a wall of the building can be made. In order to avoid sending humans into the building when the building has extremely high radiation levels, a robot is used.

Referring now to the drawings and in particular to FIG. 1, a robot system for cleaning a surface contaminated with radioactive substances is illustrated. The robot system is designated generally by the reference numeral 100. The robot system 100 includes a carriage 102 with wheels or treads enabling the robot to travel about on floors or the ground 106. Mounted on the robot 100 is a receiver/antenna unit 127 that allows remote control of the robot system 100. Remote control systems for robots are well known and details of the control system 127 are not included here. The robot system 100 can also be equipped with a camera(s) not shown, to aid in positioning the robot in relation to the surface, for example a wall 108 to be worked on.

The robot system 100 includes a system of articulated arms 112 and 116 mounted on swivels 110, 114 and 118. The articulated arm system carries a laser and a debris collection means 120. The debris collection means 120 includes a getter system to collect the ejecta/debris particles produced by the laser ablation. The getter for example can be a fluid circulation system using air or other fluid. Filtered air can be supplied to the debris collector 120 by a line 122. Fluid circulation systems are well known and include pumps, filters, and other equipment, the details of which are not included here. A vacuum line 124 will remove the ejecta particles and store the particles in container 125 in the robot 100. The container 125 can be removed and replaced by an empty container by another remote system as both the container and the robot will have become contaminated during the cleaning process.

Figure 2:
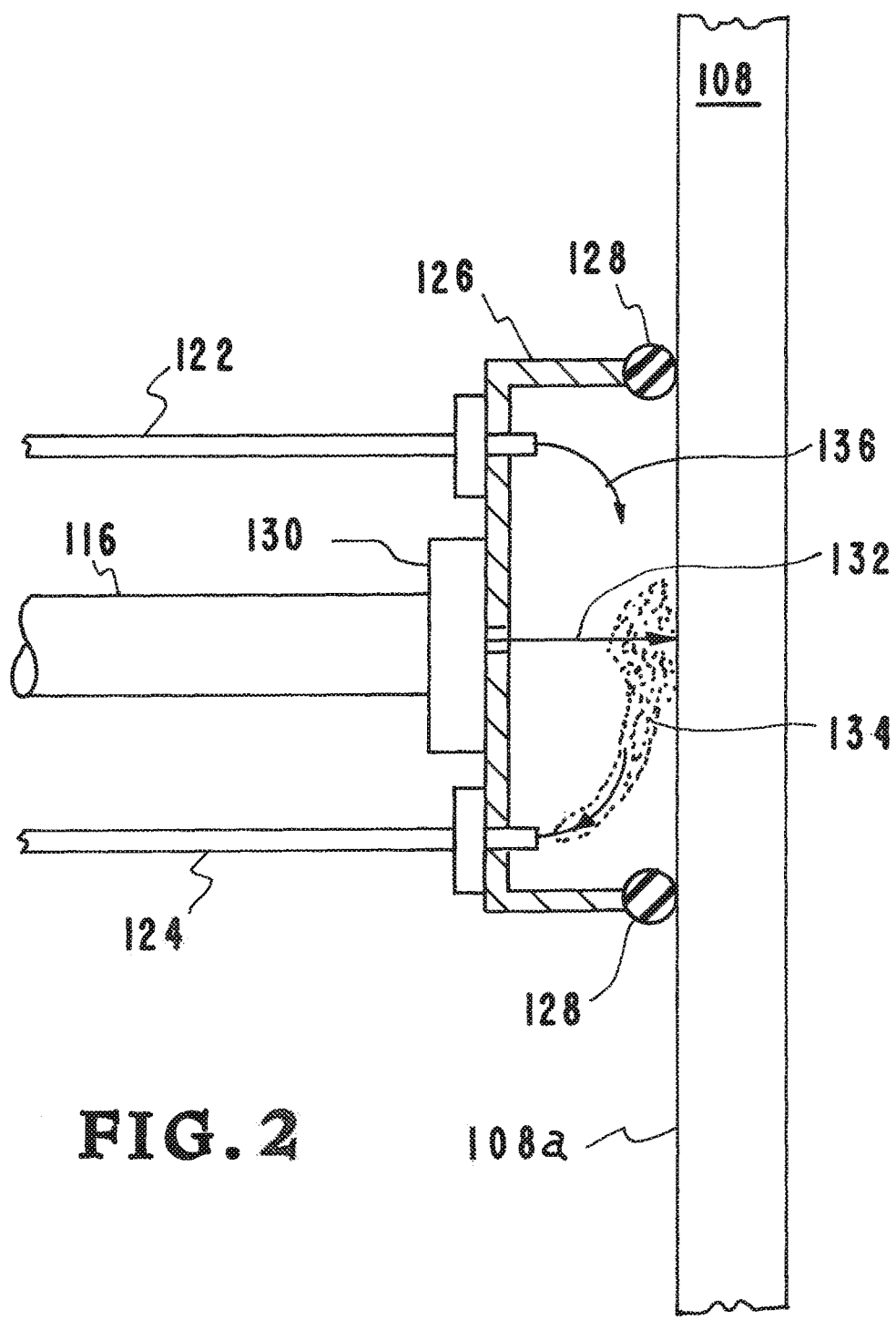
FIG. 2 illustrates a getter for collecting ejecta that is part of the robot system illustrated in FIG. 1.

Referring now to FIG. 2, the debris collection means 126 and laser 130 are shown in greater detail. A laser 130 is carried and positioned by articulated arm 116. The laser 130 produces a powerful laser beam 132 that is used to clean the surface 108*a* of the wall 108 that is contaminated with radioactive substances. The powerful laser beam 130 will ablate the wall 108 surface 108*a* producing ejecta particles 134. The ejecta particles 134 will be entrained in the getter flow 136. The debris collection unit 126 includes a getter supply line 122 and a debris collection line 124. The debris collection unit 126 also includes a seal 128 that will provide a fluid (air) tight seal between the debris collection unit 126 and the wall 108 area 108*a* being cleaned.

In a preferred embodiment the laser 130 is a solid state pulsed laser that produces a laser beam 132 of laser pulse of nano-second range incident on the surface 108*a* at some angle thereby ablating the radiation contaminated material producing the ejecta particles 134. For short pulse laser ejecta propagates in the narrow cone normal to the surface and will be caught by the compact getter 120. The laser 130 produces 20 J, 15 nsec. Pulses with 5 Hz repetition rate. The use of phase conjugation system makes it non-sensitive to vibration and misalignments. The total volume of the removed contaminant will be very small, greatly reducing the cost of the waste transportation and storage. Multiple ablations can be required for the complete decontamination.

Remediation of Biological Contaminated Surfaces

Surfaces contamination by biological material are encountered in hospitals, food processing plants, research laboratories, pharmaceutical plants, and other locations. Generally, the only surface is contaminated. Penetration can occur in concrete due to small cracks and voids. Typical decontamination includes surface cleaning or contaminated structure demolition. In both cases a dangerous contaminated waste is produced.

Figure 3:
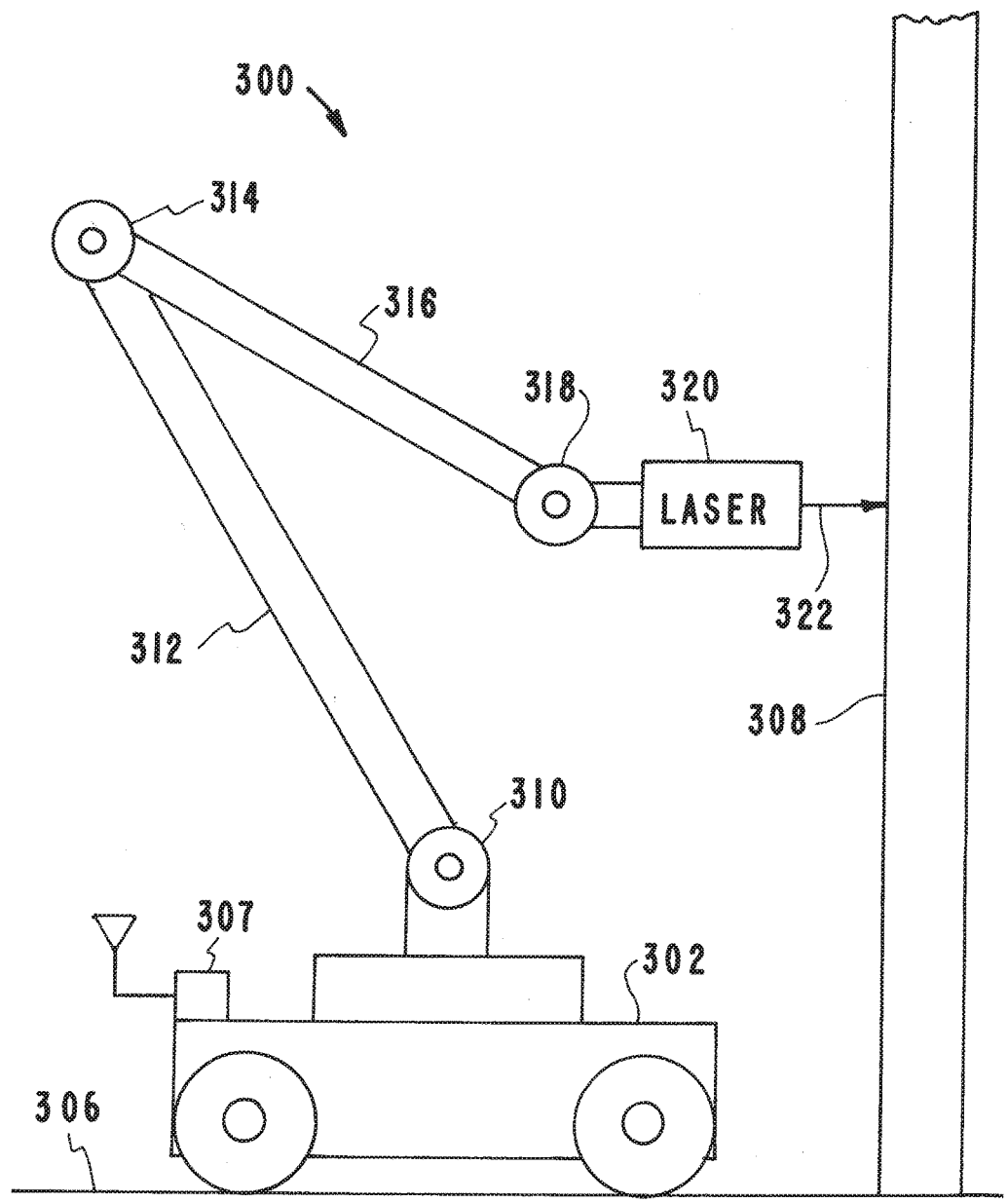
FIG. 3 illustrates a robot that can be used to clean a surface contaminated with biological material.

Referring now to the drawings and in particular to FIG. 3, a robot system for cleaning a surface contaminated with biological substances is illustrated. The robot system is designated generally by the reference numeral 300. The robot system 300 includes a carriage 302 with wheels or treads enabling the robot to travel about on floors or the ground 306. Mounted on the robot 300 is a receiver/antenna unit 307 that allows remote control of the robot system 300. Remote control systems for robots are well known and details of the control system 307 are not included here. The robot system 300 can also be equipped with a camera(s) not shown, to aid in positioning the robot in relation to the surface, for example a wall 308 to be worked on.

The robot system 300 includes a system of articulated arms 312 and 316 mounted on swivels 310, 314 and 318. The articulated arm system carries a laser 320. The laser 320 produces a laser beam 322 that is directed onto the surface of the wall 308 that is contaminated with biological substances. The laser beam can be used to heat the surface of the wall 308 to a temperature that destroys the biological material that has contaminated the surface of the wall 308. Also, the laser 320 and laser beam 322 can direct radiation onto the biological material that has contaminated the surface of the wall 308 at a wavelength that will destroy the biological material. The robot system 300 can also include a getter system such as that illustrated in FIG. 2 if there is a risk that debris or biological material will be generated.

Remediation of Chemical Contaminated Surfaces

Surfaces can become contaminate by chemicals chemical production plants, research laboratories, pharmaceutical plants and other locations. Also, in the case of a chemical weapon detonation, surfaces of structures and paved areas will be produced. Generally, only the surface is contaminated. Penetration can occur in concrete due to small cracks and voids. Typical decontamination includes surface cleaning or contaminated structure demolition. In both cases dangerous contaminated waste is produced.

Figure 4:
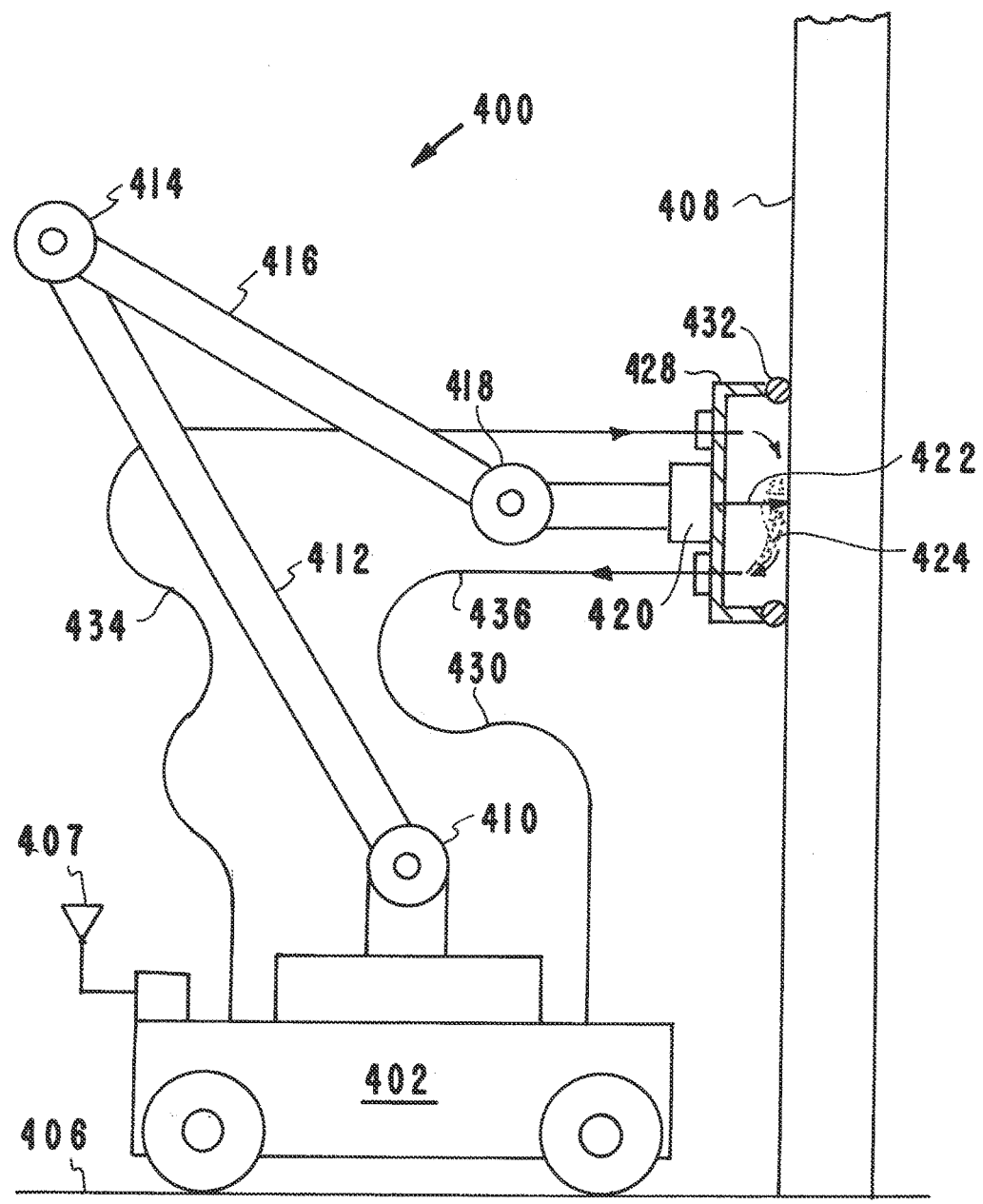
FIG. 4 illustrates a robot that can be used to clean a surface contaminated with chemicals.

Referring now to the drawings and in particular to FIG. 4, a robot system for cleaning a surface contaminated with chemical substances is illustrated. The robot system is designated generally by the reference numeral 400. The robot system 400 includes a carriage 402 with wheels or treads enabling the robot to travel about on floors or the ground 406. Mounted on the robot 400 is a receiver/antenna unit 407 that allows remote control of the robot system 400. Remote control systems for robots are well known and details of the control system 407 are not included here. The robot system 400 can also be equipped with a camera(s) not shown, to aid in positioning the robot in relation to the surface, for example a structure 408 to be worked on.

The robot system 400 includes a system of articulated arms 412 and 416 mounted on swivels 410, 414 and 418. The articulated arm system carries a laser 420. The laser 420 produces a laser beam 422 that is directed onto the surface of the structure 408 that is contaminated with chemical substances. The laser beam 422 can be used to ablate the chemical material that has contaminated the surface of the structure 408. In some instances the laser beam 422 will ablate some of the surface of the structure 408. The laser beam 422 will produce ejecta particles 424. The ejecta particles 424 can be the chemical substance or the surface material or both.

The robot system 400 includes a debris collection unit 428. The debris collection unit 428 has a recirculating fluid system that captures the ejecta particles 424. The ejecta particles 424 will be entrained in the getter flow fluid 430. The debris collection unit 428 includes a getter supply line 434 and a debris collection line 436. The debris collection unit 428 includes a seal 432 that will provide a fluid (air) tight seal between the debris collection unit 428 and the structure 408 being cleaned.

Although the description above contains many details and specifics, these should not be construed as limiting the scope of the application but as merely providing illustrations of some of the presently preferred embodiments of the apparatus, systems, and methods. Other implementations, enhancements and variations can be made based on what is described and illustrated in this patent document. The features of the embodiments described herein may be combined in all possible combinations of methods, apparatus, modules, systems, and computer program products. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination. Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described above should not be understood as requiring such separation in all embodiments.

Therefore, it will be appreciated that the scope of the present application fully encompasses other embodiments which may become obvious to those skilled in the art. In the claims, reference to an element in the singular is not intended to mean "one and only one" unless explicitly so stated, but rather "one or more." All structural and functional equivalents to the elements of the above-described preferred embodiment that are known to those of ordinary skill in the art are expressly incorporated herein by reference and are intended to be encompassed by the present claims. Moreover, it is not necessary for a device to address each and every problem sought to be solved by the present apparatus, systems, and methods, for it to be encompassed by the present claims. Furthermore, no element or component in the present disclosure is intended to be dedicated to the public regardless of whether the element or component is explicitly recited in the claims. No claim element herein is to be construed under the provisions of 35 U.S.C. 112, sixth paragraph, unless the element is expressly recited using the phrase "means for."

While the apparatus, systems, and methods may be susceptible to various modifications and alternative forms, specific embodiments have been shown by way of example in the drawings and have been described in detail herein. However, it should be understood that the application is not intended to be limited to the particular forms disclosed. Rather, the application is to cover all modifications, equivalents, and alternatives falling within the spirit and scope of the application as defined by the following appended claims.

The invention claimed is:

1. An apparatus for remediation of a radiation contaminated wall that has a radiation contaminated surface, comprising:
   a robot with a carriage having wheels or treads and a carriage body portion;
   at least one arm extending from said robot;
   a laser carried by said at least one arm, wherein said laser is a solid state pulsed laser that produces a laser beam of nano-second pulses, and wherein said laser is positioned on said at least one arm extending from said robot;
   wherein said laser is a solid state pulsed laser that produces a laser beam of nano-second pulses and wherein said solid state pulsed laser produces 20 J, 15 nsec. pulses with 5 Hz repetition rate;
   wherein said laser beam produced by said laser is directed to the radiation contaminated wall that has a radiation contaminated surface to ablate the radiation contaminated surface producing radiation contaminated particles, wherein said laser beam is positioned at an angle to the radiation contaminated surface and said laser beam strikes the radiation contaminated surface at said angle and ablates the radiation contaminated surface producing said radiation contaminated particles, and wherein said laser is positioned so that said laser beam directly strikes said radiation contaminated surface;
   an enclosed ejecta debris collection structure including a debris collection unit attached to said least one arm, said debris collection unit positioned against the radiation contaminated wall and the radiation contaminated surface to receive said radiation contaminated particles;
   a seal located between said debris collection unit and the radiation contaminated surface of said radiation contaminated wall, said seal being a fluid tight seal located between said debris collection unit and the radiation contaminated surface of said radiation contaminated wall;
   a fluid circulation system connected to said enclosed ejecta debris collection structure that collects said radiation contaminated particles;
   a container in said robot; and
   a line connected to said fluid circulation system providing a connection between said enclosed ejecta debris collection structure and said container wherein said radiation contaminated particles are directed into said container to remediate the radiation contaminated surface.

2. An apparatus for remediation of a radiation contaminated wall that has a radiation contaminated surface, comprising:
   a robot with a carriage having wheels or treads and a carriage body portion;
   a receiver/antenna unit mounted on said carriage that allows remote control of said robot;
   at least one arm extending from said robot;
   a laser carried by said at least one arm, wherein said laser is positioned on said at least one arm extending from said robot;
   a laser beam produced by said laser that is directed to the radiation contaminated surface of the radiation contaminated wall to ablate the radiation contaminated surface producing radiation contaminated particles, wherein said laser is a solid state pulsed laser that produces a laser beam of nano-second pulses, wherein said solid state pulsed laser produces 20 J, 15 nsec. pulses with 5 Hz repetition rate, wherein said laser beam is positioned at an angle to the radiation contaminated surface and said laser beam strikes the radiation contaminated surface at said angle and ablates the radiation contaminated surface producing said radiation contaminated particles, and wherein said laser is positioned so that said laser beam directly strikes said radiation contaminated surface;
an enclosed ejecta debris collection structure including a debris collection unit attached to said least one arm, said debris collection unit positioned against the radiation contaminated surface of the radiation contaminated wall to receive said radiation contaminated particles;
a seal located between said debris collection unit and the radiation contaminated surface, said seal providing a fluid tight seal between said debris collection unit and the radiation contaminated surface of the radiation contaminated wall, said seal being a fluid tight seal located between said debris collection unit and the radiation contaminated surface of said radiation contaminated wall;
a fluid circulation system connected to said enclosed ejecta debris collection structure that collects said radiation contaminated particles;
a container in said robot; and
a line connected to said fluid circulation system providing a connection between said enclosed ejecta debris collection structure and said container wherein said radiation contaminated particles are directed into said container for remediation of the radiation contaminated surface.

* * * * *